United States Patent [19]
Thiem et al.

[11] 3,969,374
[45] July 13, 1976

[54] PROCESS FOR PREPARING AMINO-ANTHRAQUINONES

[75] Inventors: Karl-Werner Thiem, Cologne; Wolfgang Auge, Odenthal-Hahnenberg; Rütger Neeff, Leverkusen, all of Germany

[73] Assignee: Bayer Aktiengesellschaft, Leverkusen, Germany

[22] Filed: Feb. 11, 1975

[21] Appl. No.: 549,120

[30] Foreign Application Priority Data
Feb. 28, 1974   Germany............................ 2409542

[52] U.S. Cl................................. 260/382; 260/378
[51] Int. Cl.$^2$.......................................... C07C 97/24
[58] Field of Search................... 260/382, 581, 378

[56] References Cited
FOREIGN PATENTS OR APPLICATIONS
2,211,411   9/1972   Germany
6,526   1878   Germany
126,542   1900   Germany

OTHER PUBLICATIONS

Lubs, The Chemistry of Synthetic Dyes & Pigments, A.C.S. Monograph, 1955, p. 361.

Barnet, Anthracene and Anthraquinone, D. Von Nostrand Co., N.Y., N.Y., 1921, pp. 195–200.

*Primary Examiner*—Arthur P. Demers
*Attorney, Agent, or Firm*—Burgess, Dinklage & Sprung

[57]   ABSTRACT

1-amino- and/or 1,5- and/or 1,8-diamino and/or 1-amino-6-nitro and/or 1-amino-7-nitro-anthraquinone are prepared by reacting 1-nitro- and/or 1,5- and/or 1,8- and/or 1,6- and/or 1,7-dinitro-anthraquinone with ammonia in the presence of a nitrile.

19 Claims, No Drawings

PROCESS FOR PREPARING AMINO-ANTHRAQUINONES

This invention relates to a process for the preparation of 1-amino-anthraquinone, 1,5- and 1,8-diamino-anthraquinone, 1-amino-6-nitro-anathraquinone and 1-amino-7-nitro-anthraquinone by reacting 1-nitro-anthraquinone, 1,5- and 1,8-dinitro-anthraquinone and 1,6- and 1,7-dinitro-anthraquinone with ammonia in the presence of nitriles.

A process for the preparation of amino-anthraquinones is described in German Offenlegungsschrift No. 2,211,411, according to which amino-anthraquinones are obtained from nitro-anthraquinones by reaction with ammonia, ammonium salts or amines in the presence of an amide which is liquid under the reaction conditions. The reaction is carried out at elevated temperatures, preferably between 100 and 180°C and optionally under pressure. The amides used are low-molecular weight organic amides, e.g. formamide, urea or N-methyl pyrrolidone.

In the aforesaid Offenlegungsschrift it is mentioned that the process is suitable not only for preparing 1-amino-anthraquinone from 1-nitro-anthraquinone but also for preparing $\alpha,\alpha$-diamino-anthraquinone or $\alpha,\beta$-diamino-anthraquinone from $\alpha,\alpha$-dinitro- or $\alpha,\beta$-dinitro-anthraquinone.

When this process is employed, 1-amino-anthraquinone and $\alpha,\alpha$-diamino-anthraquinone are obtained in only low yields and $\alpha,\beta$-dinitro-anthraquinones are predominantly converted into $\alpha$-amino-$\beta$-nitro derivatives.

SUMMARY

It has now been found that pure 1-amino-anthraquinone, 1,5-diamino- and 1,8-diamino-anthraquinone and pure 1-amino-6- or -7-nitro-anthraquinone are obtained when 1-nitro-anthraquinone or the corresponding dinitro-anthraquinones are reacted with ammonia in the presence of nitriles, preferably under pressure and at elevated temperatures. Suitable nitriles include: aliphatic, cycloaliphatic and aromatic nitriles and dinitriles, e.g. acetonitrile, adipic acid dinitrile, ethoxy propionic acid nitrile, $\alpha$-ethyl-caproic acid nitrile, azelaic acid dinitrile, benzonitrile, butyric acid nitrile, capric acid nitrile, caproic acid nitrile, caprylic acid nitrile, hydrocinnamic acid nitrile, isobutyric acid nitrile, isocaproic acid nitrile, propionic acid nitrile and n-valeric acid nitrile.

Preferred nitriles are acetonitrile and propionic acid nitrile.

The nitriles are preferably used in quantities of from 0.5 to 50 parts, by weight, per part, by weight, of nitro-anthraquinone compound, most preferably 1 to 10 parts, by weight.

In detail, the process according to the invention may, for example be carried out as follows: at a temperature of 100°- 220°C, preferably 140° - 200 C and using a molar ratio of ammonia to 1-nitro-anthraquinone (or $\alpha,\beta$-dinitro-anthraquinone) of at least 2 : 1, preferably between 8 : 1 and 40 : 1 and more particularly between 10 : 1 and 35 : 1. The molar ratio referred to herein is taken to be that of ammonia to the nitro-anthraquinones present. For the reaction of $\alpha,\alpha$-dinitro-anthraquinone it is suitable to employ molar ratios of ammonia to $\alpha,\alpha$-dinitro-anthraquinone of at least 4 : 1, preferably between 10 : 1 and 80 : 1 and, in particular, between 20 : 1 and 40 : 1. The reaction is generally carried out under pressure, in particular at pressures above 10, bar and preferably above 30 bar.

The reaction time depends on the temperature, the pressure and the molar ratio. For complete conversion, times between 2 minutes and 15 hours are required, the reaction velocity increasing with increasing temperature, increasing molar ratio and increasing pressure.

The process may be carried out continuously or discontinuously, adiabatically or isothermally at normal pressure or at excess pressure.

The reaction mixture may be worked-up by the usual methods, for example by filtering off the product which has crystallised from the organic solvent after cooling to room temperature. The mother liquor obtained may be returned to the process.

Alternatively, the reaction mixture may be worked-up by distilling off the solvent or it may be worked-up by means of a diluent (e.g. water) which reduces the solubility of the amino-anthraquinones in the reaction solution, so that the respective amino-anthraquinone precipitates. If necessary, the reaction product may be further purified by treatment with acids, for example sulphuric acid.

Since $\alpha,\alpha$-diamino-anthraquinones and $\alpha$-amino-$\beta$-nitro-anthraquinones have differing solubilities in the nitriles employed, working-up the reaction mixture may also be combined with fractional precipitation.

The mother liquor and distilled solvent obtained and the ammonia used in excess may be returned to the process. The water produced in the reaction may be removed from the cycle.

This invention relates to a particular process for the preparation of 1-amino-and/or 1,5- and/or 1,8-diamino-anthrquinone and/or 1-amino-6-nitro- and/or 1-amino-7-nitro-anthraquinone by the reaction of 1-nitro- and/or 1,5- and/or 1,8- and/or 1,6- and/or 1,7-dinitro-anthraquinone with ammonia, characterised in that the reaction is carried out in the presence of nitriles, preferably under pressure, in particular at pressures from 10 bar to 130 bar, preferably from 30 bar to 100 bar, and with molar ratios of ammonia to 1-nitro-anthraquinone and/or 1,6- and/or 1,7-dinitro-anthraquinone of at least 2 : 1, in particular between 8 : 1 and 40 : 1 and most preferably between 10 : 1 and 35 : 1, or with molar ratios of ammonia to 1,5- and/or 1,8-dinitro-anthraquinone of at least 4 : 1, preferably between 10 : 1 and 80 : 1 and in particular between 20 : 1 and 40 : 1, at elevated temperatures, preferably at 100° - 220°C and in particular at 140° - 200°C.

The process according to the invention is suitable also for preparing pure 1-amino-anthraquinone from mixtures of 1-nitro-anthraquinone and 2-nitro-anthraquinone which are obtained, for example, after removal of the dinitro-anthraquinones from the nitration products of anthraquinone. The process according to the invention acts highly preferentially on the nitro-group in the 1-position. If the reaction is stopped after complete conversion of 1-nitro-anathraquinone, a mixture of 1-amino-anthraquinone and 2-nitro-anthraquinone is obtained which may easily be separated.

One possible method of separation, for example, consists of dissolving the mixture in acids, e.g. sulphuric acid, then precipitating the 2-nitro-anthraquinone by diluting the acid with water (e.g. 50 – 70% sulphuric acid) and separating the precipitate and then precipitating 1-amino-anthraquinone from the filtrate by a further dilution and isolation.

There is also the possibility, for example, of converting 1-amino-anthraquinone into 1-thionyl-amino-anthraquinone (U.S. Pat. No. 2,479,943) which is readily soluble in organic solvents, such as benzene or toluene, and separating the slightly soluble 2-nitro-anthraquinone.

This invention therefore relates to a process for the preparation of 1-amino-anthraquinone which is substantially free from 2-amino-anthraquinone from mixtures which contain 1-nitro-anthraquinone and 2-nitro-anthraquinone, characterised in that the mixture is reacted with ammonia in the presence of nitriles, preferably under pressure, in particular at a pressure from 10 bar to 130 bar, preferably from 30 bar to 100 bar, and with a molar ratio of ammonia to 1-nitro-anthraquinone of at least 2 : 1, n particular between 8 : 1 and 40 : 1, and most preferably between 10 : 1 and 35 : 1, at elevated temperatures, preferably at 100° – 220°C and in particular at 140° – 200°C, until all the 1-nitro-anthraquinone has been converted, and the reaction product is then separated into 1-amino-anthraquinone and 2-nitro-anthraquinone.

The process according to the invention may also be employed to react nitro-anthraquinone mixtures which may contain, among other things, 1-nitro-anthraquinone and 1,5-, 1,8-, 1,6- and 1,7-dinitro-anthraquinone. The products obtained in this case may contain 1-amino-anthraquinone, 1,5- and 1,8-diamino-anthraquinone, 1-amino-6-nitro-anthraquinone and 1-amino-7-nitro-anthraquinone. Pure 1-amino-anthraquinone may easily be isolated from such products by vacuum distillation. Compared with the process disclosed in German Offenlegungsschrift No. 2,211,411, the process according to the invention has the advantage that the nitriles according to the invention do not react with the anthraquinone derivatives put into the reaction and formed in the process and that 1-amino-anthraquinone and 1,5- and 1,8-diamino-anthraquinone are obtained in considerably increased yields.

The amino-, diamino- and nitroamino-anthraquinone obtained according to the invention are important intermediates for the production of dyes.

EXAMPLE 1

A mixture of 257 g of 1-nitro-anthraquinone (98.5%, by weight) and 1 litre of acetonitrile is reacted with 340 g of ammonia in an autoclave at 80 bar and 170°C for ¼ hour (molar ratio of ammonia to 1-nitro-anthraquinone 20 : 1).

After cooling and release of pressure, the reaction product is isolated by distilling off the solvent and dried.

Yield: 227 g of a 93% 1-amino-anthraquinone (95% of the theoretical yield).

Similar yields and purities are obtained when benzonitrile, propionic acid nitrile, butyric acid nitrile, n-caproic acid nitrile, caprylic acid nitrile, isobutyric acid nitrile, isocaproic acid nitrile, n-valeric acid nitrile or mixtures of these compounds are used as solvents instead of acetonitrile.

EXAMPLE 2

275 g of 1-nitro-anthraquinone (92%) containing 7 parts, by weight, of 2-nitro-anthraquinone are heated to 180°C with 255 g of ammonia (molar ratio 15 : 1) in 1.8 litres of propionic acid nitrile in an autoclave (130 atmospheres) for ½ hour. After removal of the ammonia and solvent, 190 g of thionyl chloride are added to the reaction product in toluene in accordance with U.S. Patent Specification No. 2,479,943 and the reaction mixture is heated under reflux for 2 hours. 10 g of active charcoal are then added and the reaction mixture is filtered hot. 180 ml of methanol are added to the filtrate which is then heated to boiling for 1 hour. The precipitate formed is suction-filtered at room temperature, the filter cake is suspended in water and the toluene is driven off with steam. A hot suspension is suction-filtered, washed free from acid and dried.

Yield: 210 g of a 96% 1-amino-anthraquinone (90% of the theoretical yield).

EXAMPLE 3

After the reaction of 275 g of 1-nitro-anthraquinone (92%, 7%, by weight, of 2-nitro-anthraquinone) in 1 liter of benzonitrile with 85 g of ammonia (molar ratio 5 : 1) for 4 hours in an autoclave (130 atmospheres) at 210°C, the resulting reaction mixture is suction-filtered at room temperature and the residue is dehydrated under vacuum and dissolved in 1 litre of concentrated sulphuric acid. The solution is diluted to a 60% acid by the addition of water in the cold. After removal of the precipitate by suction filtration, the filtrate is poured on to ice. The precipitate thereby formed is suction-filtered, washed till neutral and dried.

Yield: 211 g of a 97% 1-amino-anthraquinone (92% of the theoretical yield).

EXAMPLE 4

A suspension of 256 g per hour of 1-nitro-anthraquinone (99%) in 2 litres of propionic acid nitrile per hour is continuously reacted with 255 g per hour of ammonia (molar ratio 15 : 1) at 180°C and 100 atmospheres in a reaction tube in which it has a residence time of 30 minutes. The pressure is continuously released and ammonia and propionic acid nitrile are distilled off and recycled. The residue is dried.

Yield per hour: 224 g of a 95% 1-amino-anthraquinone (95% of the theoretical yield).

EXAMPLE 5

German Offenlegungsschrift No. 2,211,411, Example 1.

26.3 g of 1-nitro-anthraquinone (96%) are suspended in 110 g of formamide. Ammonia gas is introduced at 155°C. After 4 hours, the solvent is distilled off and the residue is washed with water. After drying under vacuum, 22.5 g of a 79% 1-amino-anthraquinone (80% of the theoretical yield) are obtained.

EXAMPLE 6

A mixture of 298 g of a dinitro-anthraquinone mixture (55% 1,5-dinitro-anthraquinone, 45%, by weight, 1,8-dinitro-anthraquinone) and 3 litres of acetonitrile is reacted with 340 g of liquid ammonia in an autoclave for 1 hour at 170°C and a pressure of 44 atmospheres (molar ratio 20 : 1). After removal of excess ammonia and the solvent by distillation, the residue is dehydrated under vacuum.

Yield: 240 g (52.5%, by weight, of 1,5-diamino-anthraquinone, 96% of the theoretical yield; 40%, by weight, of 1,8-diamino-anthraquinone, 90% of the theoretical yield). Unreacted ammonia and the solvent may be returned to the process.

EXAMPLE 7

298 g of 1,5-dinitro-anthraquinone (99%, by weight) are reacted with 680 g of liquid ammonia (molar ratio 40 : 1) in 3 liters of propionic acid nitrile in an autoclave at 150°C and 50 atmospheres for 2 hours. The reaction mixture is worked-up as described in Example 6.

Yield: 238 g (96%, by weight, of 1,5-diamino-anthraquinone, 97% of the theoretical yield). Similar yields and purities are obtained when the solvents indicated in Example 1 or mixtures of these solvents are used instead of propionic acid nitrile.

EXAMPLE 8

298 g of 1,8-dinitro-anthraquinone (99%, by weight) are reacted with 1.02 kg of liquid ammonia (molar ratio 60 : 1) in 3 liters of acetonitrile in an autoclave at 80 atmospheres at 170°C for ½ hour, and when cold and having released the pressure, the reaction mixture is suction-filtered. The residue is dried.

Yield: 220 g (97%, by weight, of 1,8-diamino-anthraquinone, 91% of the theoretical yield).

EXAMPLE 9

298 g of a mixture (53.9%, by weight, of 1,5-dinitro-anthraquinone; 46.1%, by weight, of 1,8-dinitro-anthraquinone) are reacted with 102 g of liquid ammonia (molar ratio 6 : 1) in 3 litres of benzonitrile in an autoclave at 110 atmospheres and 200°C for 2 hours. After release of pressure and cooling the reaction mixture is suction-filtered and the residue is dehydrated under vacuum.

Yield: 228 g (52.5%, by weight of 1,5-diamino-anthraquinone, 93% of the theoretical yield; 42.3%, by weight, of 1,8-diamino-anthraquinone, 88% of the theoretical yield).

EXAMPLE 10

298 g of the dinitro-anthraquinone mixture indicated in Example 9 are reacted with 1.36 kg of liquid ammonia (molar ratio 80 : 1) in 2 liters of acetonitrile in an autoclave at 100°C and a pressure of 60 atmospheres for 15 hours.

The reaction mixture is poured into water. The resulting precipitate is suction-filtered, washed with water and dried.

Yield: 220 g (54%, by weight, of 1,5-diamino-anthraquinone, 93% of the theoretical yield; 46%, by weight, of 1,8-diamino-anthraquinone, 92% of the theoretical yield).

EXAMPLE 11

According to DOS No. 2,211,411.

29.8 g of a mixture (47.6%, by weight, of 1,5-dinitro-anthraquinone, 38.5%, by weight of 1,8-dinitro-anthraquinone) are suspended in 111 g of formamide. Ammonia gas is introduced at 155°C. No dinitro-anthraquinone may be detected by thin layer chromatography after 4 hours. The reaction mixture is worked-up by distilling off the formamide, washing the residue with water and then drying it.

Yield: 24.4 g (9.7%, by weight, of 1,5-diamino-anthraquinone, 21% of the theoretical yield; 20.2%, by weight, of 1,8-diamino-anthraquinone, 54% of the theoretical yield).

If the reaction is carried out under pressure at a molar ratio of 20 : 1, but under otherwise identical conditions, substantially the same result is obtained.

EXAMPLE 12

A mixture of 298 g of 1,6-dinitro-anthraquinone (99%) and 5 liters of acetonitrile is reacted with 340 g of ammonia in an autoclave at 170°C for 60 minutes (molar ratio 20 : 1, pressure 50 atmospheres). After cooling to room temperature, the reaction mixture is suction-filtered and dried.

Yield: 255 g of a 98% 1-amino-6-nitro-anthraquinone (94% of the theoretical yield).

EXAMPLE 13

The reaction described in Example 12 is carried out continuously in a reaction tube with 310 g per hour of 1,6-dinitro-anthraquinone, the pressure is released and the reaction product is dried after removal of ammonia and acetonitrile by distillation.

Yield: 269 g of a 96% 1-amino-6-nitro-anthraquinone (97% of the theoretical yield).

EXAMPLE 14

A mixture of 298 g of 1,7-dinitro-anthraquinone (99%) and 3 liters of propionitrile is reacted with 510 g of ammonia (molar ratio 30 : 1, pressure 60 atmospheres) in an autoclave at 140°C for 4 hours. 260 g of a 97% 1-amino-7-nitro-anthraquinone (95% of the theoretical yield) are obtained after working-up as described in Example 12.

EXAMPLE 15

Ammonia is passed through a mixture of 257 g of 1-nitro-anthraquinone (98.5%, by weight) and 1 liter of benzonitrile at 170°C/1 bar until no more 1-nitro-anthraquinone may be detected (about 4 hours).

After removal of the solvent by distillation, the residue is dried in a high vacuum.

Yield: 227 g of a 93% 1-amino-anthraquinone (95% of the theoretical yield).

What is claimed is:

1. Process for preparing 1-amino- and/or 1,5- and/or 1,8-diamino and/or 1-amino- 6-nitro- and/or 1-amino-7-nitro-anthraquinone which comprises reacting 1-nitro-and/or 1,5- and/or 1,8- and/or 1,6- and/or 1,7-dinitro anthraquinone with ammonia in the presence of a nitrile.

2. Process of claim 1 wherein the reaction is carried out in the process of from 0.5 to 50 parts, by weight, of nitrile per part, by weight, of nitro- and/or dinitro-anthraquinone.

3. Process of claim 1 wherein the reaction is carried out at a temperature of from 100° to 220°C.

4. Process of claim 3 wherein the temmperature is from 140° to 200°C.

5. Process of claim 1 wherein the reaction is carried out under a pressure from 10 bar to 130 bar.

6. Process of claim 5 wherein the pressure is from 30 bar to 100 bar.

7. Process of claim 1 wherein the reaction of 1-nitro- and/or 1,6- and/or 1,7- dinitro anthraquinone is carried out using a mole ratio of ammonia to 1-nitro anthraquinone of at least 2 : 1.

8. Process of claim 7 wherein the ratio is between 8 : 1 and 40 : 1.

9. Process of claim 8 wherein the ratio is between 10 : 1 and 35 : 1.

10. Process of claim 1 wherein the reaction of 1,5- and/or 1,8- dinitro anthraquinone is carried out using a molar ratio of ammonia to 1,5- and/or 1,8- dinitro-anthraquinone of at least 4 : 1.

11. Process of claim 10 wherein the ratio is between 10 : 1 and 80 : 1.

12. Process of claim 11 wherein the ratio is between 20 : 1 and 40 : 1.

13. Process for preparing 1-amino anthraquinone substantially free from 2-amino anthraquinone from a mixture of 1-nitro- and 2-nitro-anthraquinone which comprises adding ammonia to the mixture in a molar ratio of at least 2 : 1, based on the 1-nitro-anthraquinone, to ensure substantially complete amination of the 1-nitro anthraquinone, the reaction being carried out in the presence of a nitrile at an elevated temperature, and subsequently separating the 1-amino-anthraquinone from the reaction mixture comprising 2-nitro-anthraquinone.

14. Process of claim 13 wherein the reaction is carried out in the presence of from 0.5 to 50 parts, by weight, of nitrile per part, by weight, of nitro-anthraquinone.

15. Process of claim 13 wherein the reaction is carried out at a temperature of from 100 to 220°C.

16. Process of claim 13 wherein the temperature is from 140° to 200°C.

17. A process according to claim 1 wherein said nitrile is an aliphatic, cycloaliphatic or aromatic nitrile or dinitrile.

18. A process according to claim 18 wherein said nitrile is selected from the group concisting of acetonitrile, adipic acid dinitrile, ethoxy propionic acid nitrile, α-ethylcaproic acid nitrile, azelaic acid dinitrile, benzonitrile, butyric acid nitrile, capric acid nitrile, caproic acid nitrile, caprylic acid nitrile, hydrocinnamic acid nitrile, isobutyric acid nitrile, isocaproic acid nitrile, propionic acid nitrile and n-valeric acid nitrile.

19. A process according to claim 18 wherein said nitrile is acetonitrile or propionic acid nitrile.

* * * * *